United States Patent
Lipkens et al.

(10) Patent No.: US 9,556,411 B2
(45) Date of Patent: *Jan. 31, 2017

(54) ULTRASOUND AND ACOUSTOPHORESIS FOR COLLECTION AND PROCESSING OF OLEAGINOUS MICROORGANISMS

(71) Applicants: Bart Lipkens, Hampden, MA (US); Eric Mitchell, Bonita Springs, FL (US); Joey Carmichael, Hermon, ME (US); Dane Mealey, Springfield, MA (US); Jason Dionne, Simsbury, CT (US)

(72) Inventors: Bart Lipkens, Hampden, MA (US); Eric Mitchell, Bonita Springs, FL (US); Joey Carmichael, Hermon, ME (US); Dane Mealey, Springfield, MA (US); Jason Dionne, Simsbury, CT (US)

(73) Assignee: FloDesign Sonics, Inc., Wilbraham, MA (US)

( * ) Notice: Subject to any disclaimer, the term of this patent is extended or adjusted under 35 U.S.C. 154(b) by 297 days.

This patent is subject to a terminal disclaimer.

(21) Appl. No.: 14/090,684

(22) Filed: Nov. 26, 2013

(65) Prior Publication Data

US 2014/0080207 A1 Mar. 20, 2014

Related U.S. Application Data

(63) Continuation of application No. 13/216,095, filed on Aug. 23, 2011, now Pat. No. 8,592,204.
(Continued)

(51) Int. Cl.
*C12M 1/00* (2006.01)
*B01L 1/00* (2006.01)
(Continued)

(52) U.S. Cl.
CPC .............. *C12M 47/06* (2013.01); *C12M 21/02* (2013.01); *C12M 33/08* (2013.01); *C12M 47/02* (2013.01); *C12M 47/10* (2013.01); *C12N 13/00* (2013.01)

(58) Field of Classification Search
CPC ....... C12M 47/06; C12M 21/02; C12M 33/08; C12M 47/02; C12M 47/10; C12M 35/04; C12N 13/00
(Continued)

(56) References Cited

U.S. PATENT DOCUMENTS 4,065,875 A * 1/1978 Srna ........................ A01G 33/00
                                                                    210/748.03
4,165,273 A     8/1979 Azarov et al.
(Continued)

FOREIGN PATENT DOCUMENTS

WO    WO-2009111276 A1    9/2009

OTHER PUBLICATIONS

Extended European Search Report for Application No. EP 12833859.7.
(Continued)

*Primary Examiner* — Nathan Bowers
(74) *Attorney, Agent, or Firm* — Richard M. Klein; Fay Sharpe LLP

(57) ABSTRACT

Microorganisms such as microalgae are collected and separated from a host medium such as water. Cellular walls and membranes of the microorganisms are then ruptured to release their lipids using a lipid extraction unit. Thereafter, the lipids from the host medium are collected and separated using a lipid collection and separation unit. Related apparatus, systems, techniques and articles are also described.

16 Claims, 19 Drawing Sheets

Related U.S. Application Data

(60) Provisional application No. 61/402,076, filed on Aug. 23, 2010.

(51) Int. Cl.
    *C12N 13/00*      (2006.01)
    *C12M 1/26*      (2006.01)

(58) Field of Classification Search
    USPC .................................................. 435/306.1
    See application file for complete search history.

(56) References Cited

U.S. PATENT DOCUMENTS

| | | | |
|---|---|---|---|
| 4,398,325 A | 8/1983 | Piaget et al. | |
| 5,085,783 A * | 2/1992 | Feke | B01D 21/283 210/243 |
| 5,164,094 A * | 11/1992 | Stuckart | B01D 21/283 204/157.15 |
| 5,225,089 A | 7/1993 | Benes et al. | |
| 6,166,231 A | 12/2000 | Hoeksema | |
| 6,482,327 B1 * | 11/2002 | Mori | C02F 9/00 204/155 |
| 6,487,095 B1 | 11/2002 | Malik et al. | |
| 7,541,166 B2 | 6/2009 | Belgrader et al. | |
| 2002/0134734 A1 | 9/2002 | Campbell et al. | |
| 2003/0230535 A1 | 12/2003 | Affeld et al. | |
| 2004/0124155 A1 * | 7/2004 | Meegan, Jr. | B01D 51/08 95/29 |
| 2005/0196725 A1 | 9/2005 | Fu | |
| 2007/0272618 A1 | 11/2007 | Gou et al. | |
| 2010/0000945 A1 | 1/2010 | Gavalas | |
| 2010/0261918 A1 | 10/2010 | Chianelli et al. | |
| 2010/0317088 A1 | 12/2010 | Radaelli et al. | |
| 2010/0330633 A1 | 12/2010 | Walther et al. | |
| 2011/0003350 A1 | 1/2011 | Schafran et al. | |
| 2011/0095225 A1 | 4/2011 | Eckelberry et al. | |
| 2011/0123392 A1 * | 5/2011 | Dionne | C12M 47/02 210/748.05 |
| 2011/0166551 A1 | 7/2011 | Schafer | |
| 2013/0115664 A1 * | 5/2013 | Khanna | C12M 21/02 435/292.1 |
| 2013/0217113 A1 * | 8/2013 | Srinivasan | C12M 47/06 435/306.1 |

OTHER PUBLICATIONS

Pangu et al.; Droplet transport and coalescence kinetics in emulsions subjected to acoustic fields; ScienceDirect Ultrasonics 46; 2007; pp. 289-302.

Garcia-Lopez, A., et al., "Enhanced Acoustic Separation of Oil-Water Emulsion in Resonant Cavities." The Open Acoustics Journal. 2008, vol. 1, pp. 66-71.

B. Lipkens, J. Dionne, A. Trask, B. Szczur, A. Stevens, and E. Rietman, "Separation of micron-sized particles in macro-scale cavities by ultrasonic standing waves," Presented at the International Congress on Ultrasonics, Santiago, Jan. 11-17, 2009.

B. Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008.

B. Lipkens, M. Costolo, and E. Rietman, "The effect of frequency sweeping and fluid flow on particle trajectories in ultrasonic standing waves," IEEE Sensors Journal, vol. 8, No. 6, pp. 667-677, 2008.

Castro, V. E., "Tunable gap and quantum quench dynamics in bilayer graphene"; Jul. 13, 2010, Mathematica Summer School.

International Search Report and Written Opinion dated Dec. 2011, for corresponding PCT application No. PCT/US2011/032181.

International Search Report and Written Opinion dated Feb. 27, 2012, for PCT application No. PCT/US2011/040787.

L. P. Gor'Kov, "On the forces acting on a small particle in an acoustical field in an ideal fluid," Soy. Phys. Dokl., vol. 6, pp. 773-775, 1962.

Meribout, et al., "An Industrial-Prototype Acoustic Array for Real-Time Emulsion Layer Detection in Oil Storage Tanks", IEEE Sensors Journal, vol. 9, No. 12, Dec. 2009.

Pangu et al., "Droplet transport and coalescence kinetics in emulsions subjected to acoustic fields", Ultrasonics 46, pp. 289-302 (2007).

Ponomarenko et al., "Density of states and zero Landau level probed through capacitance of graphene"; Nature Nanotechnology Letters; Jul. 5, 2009; DOI: 10.1038/NNANO.2009.177.

Sony News Release : <http://www.sony.net/SonyInfo/News/Press/201010/10-137E/index.html>.

Cravotto et al., Ultrasonics Sonochemistry, vol. 15, No. 5, p. 898-902, 2008.

Alvarez et al., Shock Waves, vol. 17, No. 6, p. 441-447, 2008.

\* cited by examiner

800

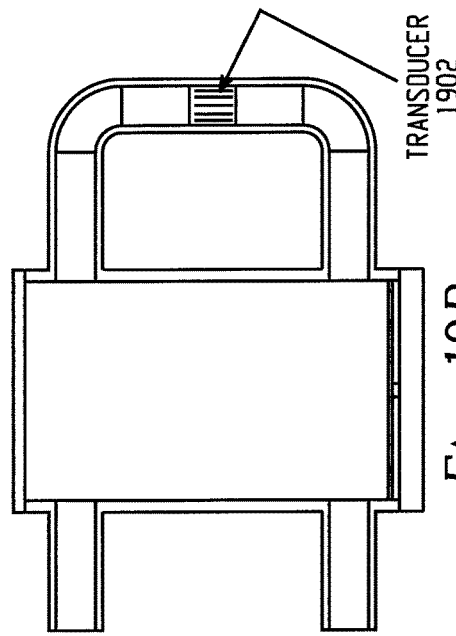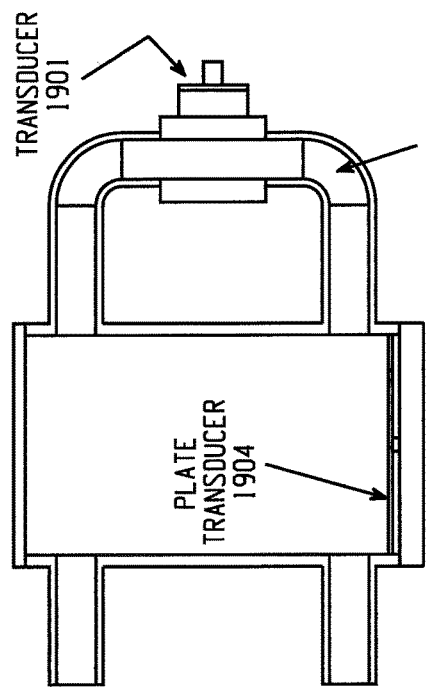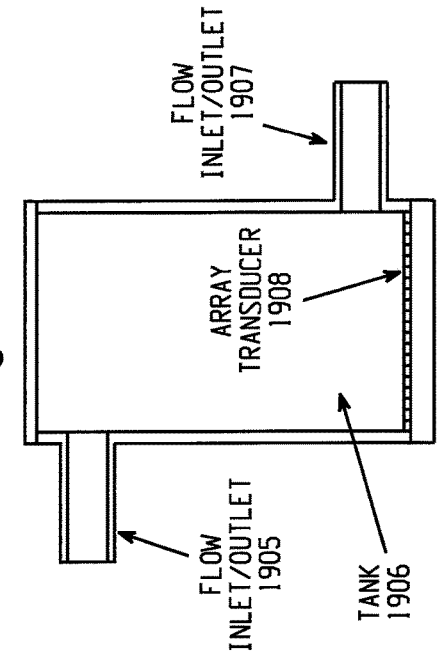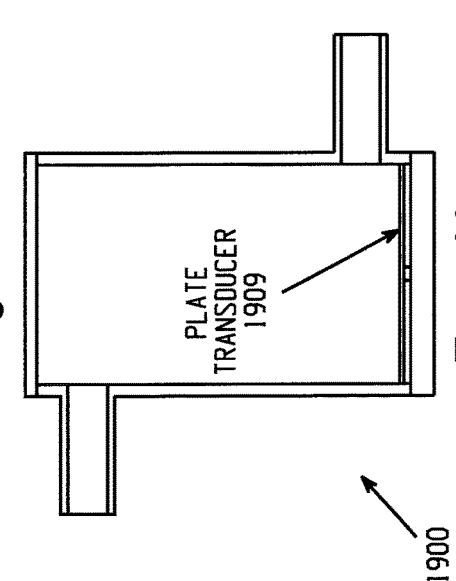

ULTRASOUND AND ACOUSTOPHORESIS FOR COLLECTION AND PROCESSING OF OLEAGINOUS MICROORGANISMS

RELATED APPLICATION

This application is a continuation of U.S. patent application Ser. No. 13/216,095, filed on Aug. 23, 2011, which claims priority to U.S. patent application Ser. No. 61/402,076 filed on Aug. 23, 2010, the contents of which are hereby fully incorporated by reference.

TECHNICAL FIELD

The subject matter described herein relates to systems and techniques for the collection and processing of oleaginous microorganisms for application such as biooil that uses ultrasound and acoustophoresis.

BACKGROUND

Biofuels, such as biodiesel, that can be produced from biooil feedstocks that are in turn produced by oleaginous microorganisms, such as microalgae, bacillus, fungi, and yeast are increasingly being adopted. Oleaginous microorganisms are microbial with lipid content typically in excess of 20%. A renewable liquid fuel energy source could play a significant role in reducing our national dependence on foreign oil imports. Reported in the literature is that oleaginous yeasts and microalgae can grow and accumulate significant amounts of lipids (see A. Banerjee, R. Sharma, Y. Chisti and U. C. Banerjee, "Botryococcus Braunii: A renewable source of hydrocarbons and other chemicals" Critical Reviews in Biotechnology, 22 (3), 245-279, 2002; Y. Chisti, "Biodiesel from microalgae beats bioethanol" Trends in Biotechnology, 26 (3), 126-131, 2007; P. Metzger and C. Largeau, "Botryococcus braunii: a rich source for hydrocarbons and related ether lipids" Appl. Microbiol. Biotechnol, 66, 486-496, 2005; X. Meng, J. Yang, X. Xu, L. Zhang, Q. Nie, M. Xian "Biodiesel production from oleaginous microorganisms" Renewable Energy, 34, 1-5, 2009, the contents of each of the aforementioned papers being incorporated by reference). The oil content and composition are a function of the type of microorganisms used and the conditions in which the culturing took place. As an example, microalgae are sunlight driven cell factories that convert carbon dioxide to potential biofuels. Microalgae grow at a very fast pace, doubling their biomass within a 24 hour time period and are rich in oil. The lipid content of microalgae can be as high as 70%. In particular, microalgae are reported to be excellent candidates for biodiesel production because of their higher biomass production, higher photosynthetic efficiency, and faster growth compared to most other energy crops.

Most of the work reported in the literature on the development of microbial oil production has focused on the identification of better strains of oleaginous microorganisms, on genetic and metabolic engineering of strains, on the development of the optimal environmental conditions for microorganism growth, and on the development of the optimal energy sources to fuel the growth of the microorganisms.

Similar to the biofuel studies there have been studies on chemical and nutraceutical production in microalgae (see J. N. Rosenberg, G. A. Oyler, L. Wilkinson and M. J. Betenbaugh, "A green light for engineered algae: redirection metabolism to fuel a biotechnology revolution", Current Opinion in Biotechnology, 19, 430-436, 2008, the contents of which are hereby incorporated by reference). However there has been little effort spent on the harvesting of microorganisms, particularly from large-scale (100 liter to 2 million liter) volume cultures. Therefore, significant challenges remain in the energy efficient and economical harvesting of microorganisms from their host medium, as well as steps to collect the microbial oils. In particular, harvesting of the microorganisms by the concentration and separation of the microorganisms from their host medium, typically water.

Algae use in bioreactors or large ponds is increasingly being employed for biofuels and nutraceuticals. Metzger, and Largeau (2005) and Banerjee (2002) describe the use of *Botryococcus braunii* as a source of hydrocarbons and similar lipids, such as $C_{27}$diane, $C_{30}$ botryococcene, squalene, tetramethylsqualene and trs,trs-lycopadine, among others including ether lipids, epoxides and sterols. Weldy and Huesemann (C. S. Weldy and M. Huesemann, "Lipid production by *Dunaliella salina* in batch culture: effects of nitrogen limitation and light intensity" U.S. Department of Energy Journal of Undergraduate Research, Vol. VII, 115-122, 2007) and Hejazi and Wijffels (M. A. Hejazi and R. H. Wijffels, "Effect of light intensity on beta-carotene production and extraction by *Dunaliella salina* in two-phase bioreactors" Biomolecular Engineering, 20, 171-175, 2003) describe the use of *Dunaliella salina*, for lipid production and beta-carotene production. Other researchers, including Chisti (2007), Meng et al. (2009) and Hu (Q. Hu, M. Sommerfeld, E. Jarvis, M. Ghirardi, M. Posewitz, M. Seibert, and A. Darzins, "Microalgae triacylglycerols as feedstocks for biofuel production: perspectives and advances" The Plant Journal, 54, 621-639, 2008) discuss the use of microalgae for biodiesel and triacylglycerols production. Lastly, Rosenberg et al (2008) describe a whole list of nutraceuticals, pharmaceuticals, and high-value chemicals produced from microalgae. In all these applications, there is a need for improved algae concentrating, or as is known, dewatering. Conventional techniques involve batch centrifuging at high-cost.

SUMMARY

In one aspect, an apparatus is provided that includes a microorganism collection and separation unit, a lipid extraction unit, and a lipid collection and separation unit. The microorganism collection and separation unit can include a first flow chamber that in turn comprises a first inlet through which is flowed a mixture of a host fluid and microorganisms along a first flow path, a first outlet, and at least one first ultrasonic transducer forming a standing acoustic wave substantially perpendicular to the first flow path to selectively separate the microrganisms from the host fluid so that such microorganisms are collected and remaining host fluid exits the first flow chamber via the first outlet. The lipid extraction unit can include a second flow chamber that in turn comprises a second inlet through which is flowed a mixture of a host fluid and microorganisms collected by the microorganism and separation unit along a second flow path, a second outlet, and at least one second ultrasonic transducer forming a standing acoustic wave substantially perpendicular to the second flow path to selectively rupture cellular walls and membranes of the microrganisms to release lipids, the lipids being collected and remaining host fluid exiting the second flow chamber via the second outlet. The lipid collection and separation unit can include a third flow chamber that in turn comprises a third inlet through which is flowed a mixture of a host fluid and lipids from the lipid extraction unit along a third flow path, a third outlet, and at least one third ultrasonic transducer forming a standing acoustic wave substantially perpendicular to the third flow path to selectively separate the lipids from the host fluid so that such lipids are collected and remaining host fluid exits the third flow chamber via the third outlet.

The standing acoustic wave can direct the microorganisms to at least one collection pocket for collection and removal from the first flow chamber. Similarly, the standing acoustic wave directs the lipids to at least one collection pocket for collection and removal from the third flow chamber.

The microorganisms can be selected from a group consisting of: microalgae, yeast, fungi, bacteria, and spores. Each transducer can be optimized for a specific range of particles selected from a group consisting of microalgae, yeast, fungi, bacteria, and spores.

One or more of the first, second, and/or third ultrasonic transducer(s) can operate at a frequency in a range of 1 MHz to 10 MHz. The ultrasonic transducers can be driven at a constant frequency of excitation or a frequency sweep pattern. The second transducer can be driven by a pulsed waveform that does not result in cavitation of the microorganisms. Conversly, the second ultrasonic transducer can be driven by a waveform (e.g., an arbitrary waveform) that results in cavitation of the microorganisms. One or more of the first, second, and/or third ultrasonic transducer(s) can be embedded in a wall of the corresponding flow chamber.

The lipid extraction unit can also include a recirculation unit comprising a tank, an inlet, and outlet, and at least one recirculation arm. The tank can include at least one plate transducer and/or at least one array transducer. The recirculation arm can include a flat transducer and/or a ring transducer. The lipid collection and separation unit can cause the lipids to agglomerate such that their buoyancy force is sufficient to force the lipids to float to the top of the third flow chamber to result in a lipid layer which can then be collected.

In an interrelated aspect, a method is provided in which microorganisms are collected and separated from a host medium (e.g., water, etc.) using a microorganism collection and separation unit. Thereafter, cellular walls and membranes of the microorganisms are ruptured using a lipid extraction unit in order to release their lipids. Subsequently, the lipids are collected and separated from the host medium using a lipid collection and separation unit.

In a further interrelated aspect, a system is provided that comprises three subsystems including a first subsystem for the trapping, concentration, collection, and separation of microorganisms such as microalgae, yeast, fungi, bacteria, or spores from a host medium such as water, a second subsystem for the rupturing of the cell wall and cellular membranes of the microorganism such that the lipid content of the microorganism is released into the water, typically in the form of microscopic oil droplets, and a third subsystem for the concentration, collection, and separation of oil droplets from an oil/water emulsion, where the oil droplets are the lipids of said microorganisms, and where the separation of the oil droplets results in an oil layer, which can then be harvested as a feedstock for the production of biofuels or for other uses (e.g., carotenes as food supplements). The first subsystem to trap, concentrate, collect, and separate the microorganisms from water employs a flow chamber through which the mixture flows, and an ultrasonic transducer, embedded in the flow chamber wall, which, in combination with an acoustic reflector typically located at the wall opposite the transducer face, generates an acoustic standing wave in the water and acts as a trap for the microorganisms in the acoustic field through the action of the acoustic radiation force. The second subsystem employs an ultrasonic transducer, embedded in the wall of a tank or a flow through channel, which generates high intensity ultrasound with or without cavitation effects sufficient to rupture the cell wall of the microorganisms resulting in the release of the lipid content of the microorganism into the water, resulting in an oil/water emulsion. The third subsystem employs a flow-through chamber through which the oil water emulsion flows and an ultrasonic transducer embedded in the flow chamber wall, which, in combination with an acoustic reflector typically located at the wall opposite the transducer face, generates an acoustic standing wave in the emulsion that acts as a trap for the microscopic oil droplets through the action of the acoustic radiation force. The trapping of the oil droplets results in the coalescence and aggregation of the oil droplets into large aggregates of oil droplets such that buoyancy forces the aggregates to rise to the top of the flow channel, where the lipids form an oil layer which can then be harvested as feedstock for the production of biofuels or for other uses (e.g., carotenes as food supplements).

The current subject matter provides many advantages. For example, the current subject matter enables the processing of large quantities of a host medium, e.g., water, which is laden with oleaginous microorganisms by efficiently trapping, concentrating, and separating the microorganisms from the host medium. This is accomplished by rupturing the cell walls and cellular membranes of the microorganisms so that the microbial lipids (i.e., biooils, etc.) that are contained within the oleaginous microorganisms are released into the host medium.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 19A-D are diagrams illustrating variations of an apparatus for the processing of microorganisms.

DETAILED DESCRIPTION

Figure 1:
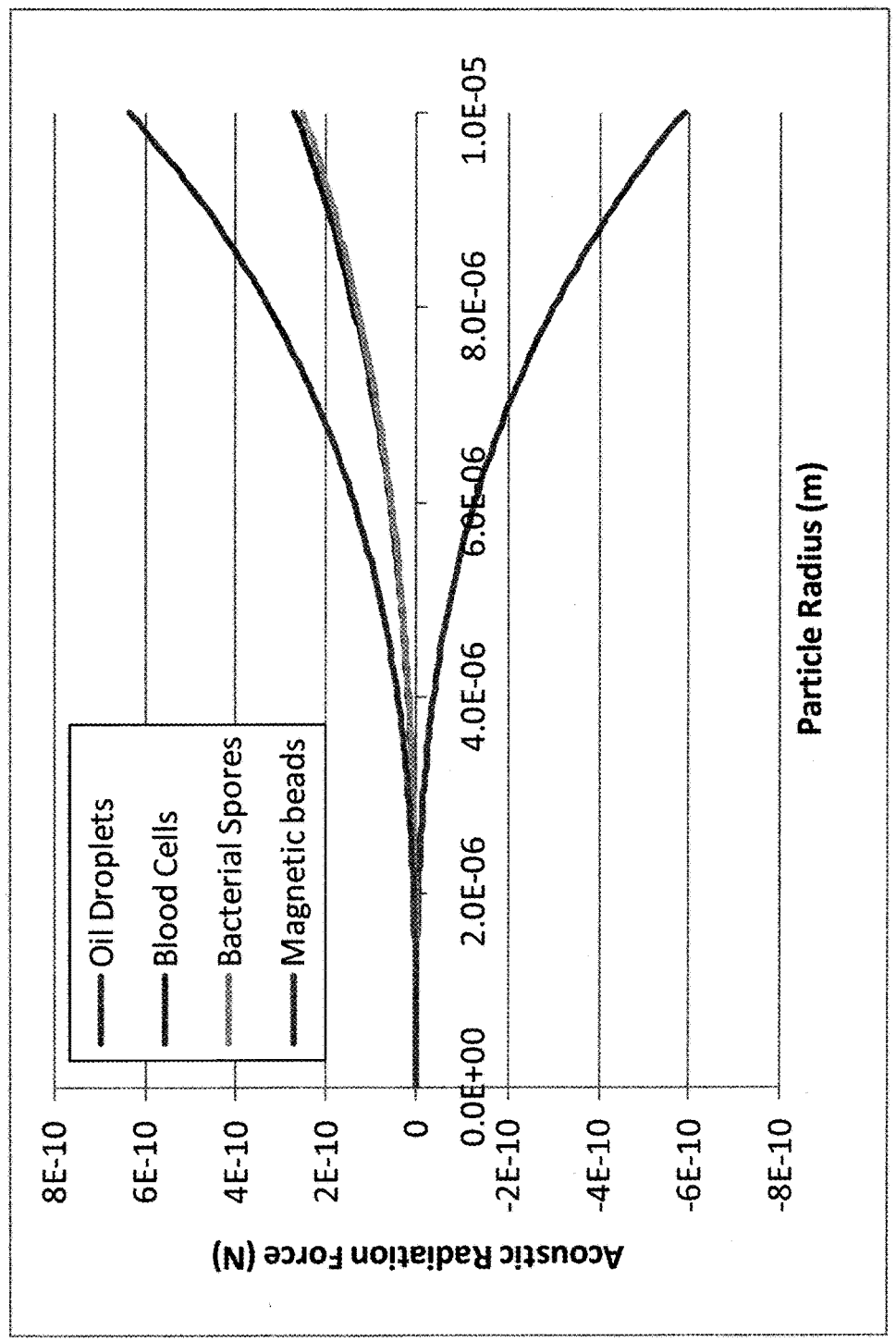
FIG. 1 is a diagram illustrating calculated acoustic force operating on micron-size particles as a function of the particle (or droplet) radius at a frequency of 1 MHz and acoustic pressure amplitude of 0.5 MPa.
Figure 2:
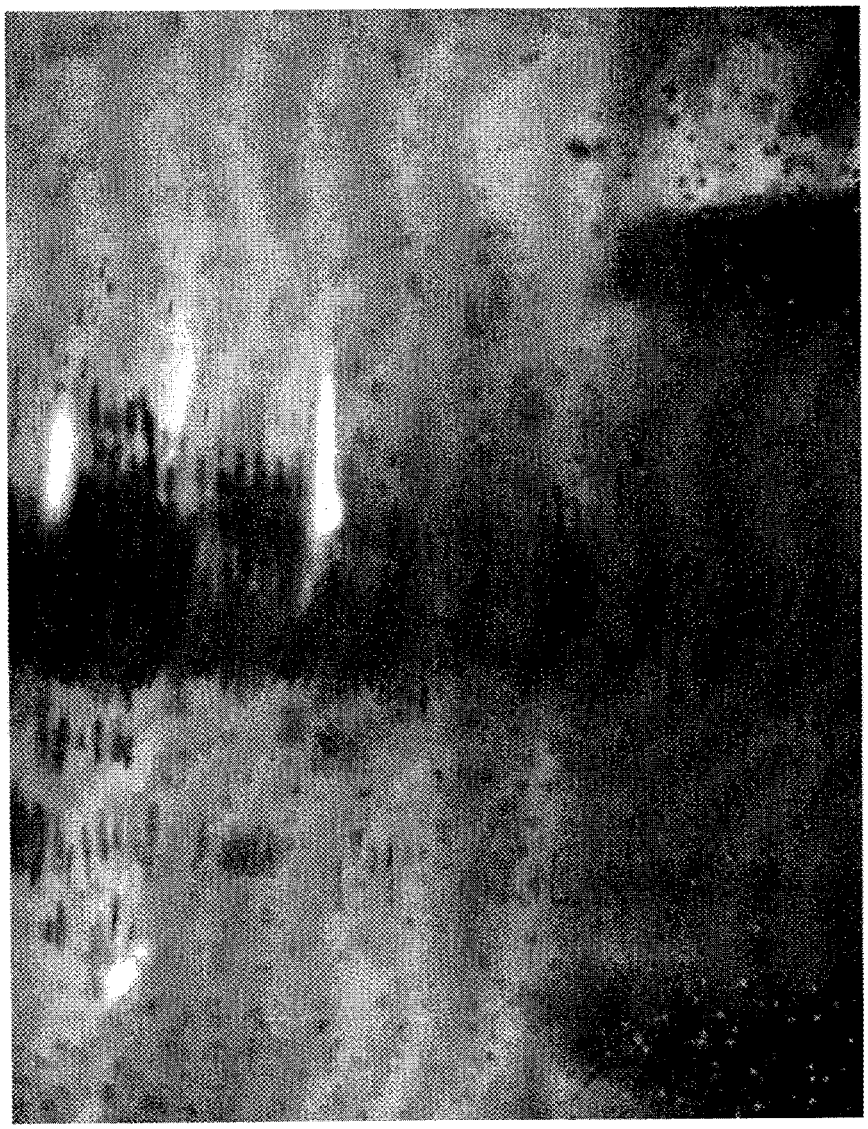
FIG. 2 is a photomicrograph of acoustophoretic trapping of the algae *Dunaliella salina* in flowing water in which the transducer is at the top, just out of the image; the column of trapped algae is about 2.5 cm high×1 cm wide, and where the ultrasonic pressure nodes are seen as the horizontal planes in which the algal cells are captured; the water flow is from left to right.

The current subject matter utilizes acoustophoresis, a low-power, no-pressure-drop, no-clog solid-state approach to particle removal from fluid dispersions: i.e., it is used to achieve separations that are more typically performed with porous filters and centrifuges, but it has none of the disadvantages of these systems. For example, the diagram 100 of FIG. 1 shows the forces for an applied acoustic frequency of 1 MHz (typical for an ultrasonic transducer) and an acoustic pressure of 0.5 MPa maximum at the antinodes (readily achieved in water). Achievement of higher applied acoustic frequencies and higher acoustic pressures will require better impedance matching. Examples of acoustic filters utilizing acoustophoresis can be found in commonly owned U.S. patent application Ser. Nos. 12/947,757, 61/261,686, 13/085,299 and 61/342,307, the contents of all of these applications are hereby fully incorporated by reference.

The acoustic radiation force ($F_{ac}$) acts on the secondary-phase particles (or fluid droplets), pushing them to the nodes (or antinodes) of the acoustic standing wave. The magnitude of the force depends on the particle density and compressibility relative to the fluid medium, and increases with the particle volume. The diagram 100 of FIG. 1 illustrates the acoustic force that operates on four different secondary phases in water as a function of the particle (or droplet) radius. The four secondary phases are hexanes (a mixture of hydrocarbons, a model for oils), red blood cells (a model for biological cells), bacterial spores (a model for "large" protein clusters and polystyrene beads such as are used for flow cytometry), and paramagnetic polystyrene beads (used for various biological capture and separation protocols). Parameters used in the calculation of the acoustic force are given below are in Table 1 (which are of particular interest regarding the algae parameters).

The current subject matter is advantageous in that it uses acoustophoresis for separations in extremely high volumes and in flowing systems with very high flow rates. Separations have been done for micron-size particles, for which the acoustophoretic force is quite small. For example, B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009; and B. Lipkens, J. Dionne, M. Costolo, A. Stevens, and E. Rietman, "Separation of bacterial spores from flowing water in macro-scale cavities by ultrasonic standing waves", (Arxiv) June 2010, the contents of both papers are hereby fully incorporated by reference) show that *Bacillus cereus* bacterial spores (a model for anthrax) have been trapped at 15% efficiency in an acoustophoretic cavity embedded in a flow system that can process drinking water at rates up to 120 mL/minute (1 cm/second linear flow). The concentration ratio has been as high as 1000 in a single-pass, small-scale prototype acoustocollector. However, the techniques described in this paper do not always scale up to higher flow rates.

An acoustophoretic separator can be created by using a piezoelectric acoustic transducer and an opposing reflection surface (or a second transducer) to set up a resonant standing wave in the fluid of interest. The ultrasonic standing waves create localized regions of high and low pressure, corresponding to high and low density of the fluid. Secondary phase contaminants are pushed to the standing wave nodes or antinodes depending on their compressibility and density relative to the surrounding fluid. Particles of higher density and compressibility (e.g., bacterial spores) move to the nodes in the standing waves; secondary phases of lower density (such as oils) move to the antinodes. The force exerted on the particles also depends on their size, with larger particles experiencing larger forces.

Diagram 200 of FIG. 2 shows the acoustophoretic collection of algae in a flowing water stream. A flat, circular transducer can, for example, be used in an acoustocollector to generate the collected matter in FIG. 1. The pressure field of such a transducer is a Bessel function that has a radial component in addition to the linear standing wave. The radial component acts to hold the captured algae in the column against the fluid flow. The trapped algae are then further concentrated in region by gravitational settling or by being driven to a collector pocket through a slow frequency sweeping method similar to that given in (i) B. Lipkens, M. Costolo, and E. Rietman, "The effect of frequency sweeping and fluid flow on particle trajectories in ultrasonic standing waves", IEEE Sensors Journal, Vol. 8, No. 6, pp. 667-677, 2008; (ii) Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008; and (iii) B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A). The contents of each of the aforementioned papers are hereby fully incorporated by reference.

Physics of acoustophoresis. Acoustophoresis is the separation of a second phase (or phases) from a host fluid using sound pressure to create the driving force. An ultrasonic transducer operating at a fixed frequency f (Hz) is used to set up an acoustic standing wave in a fluid-filled cavity. The standing wave is characterized by a local pressure p that is a function of position (x) and time (t), $$p(x,t) = P\cos(kx)\sin(\omega t) \quad (1)$$

where P is the amplitude of the acoustic pressure; k is the wavenumber ($=2\pi/\lambda$, where $\lambda$ is the wavelength), and $\omega=2\pi f$, where $\omega$ is the angular frequency. The pressure of the acoustic wave produces an acoustic radiation force $F_{ac}$ on secondary-phase elements according to $$F_{ac} = X\pi R_p^3 k \frac{P^2}{\rho_f c_f^2} \sin(2kx), \quad (2)$$

where $R_p$ is the particle radius, $\rho_f$ is the density of the fluid medium, $c_f$ is the speed of sound in the fluid, and X is the acoustic contrast factor, defined by $$X = \frac{1}{3}\left[\frac{5\Lambda-2}{1+2\Lambda} - \frac{1}{\sigma^2\Lambda}\right], \quad (3)$$

where $\Lambda$ is the ratio of the particle density to fluid density and $\sigma$ is the ratio of the speed of sound in the particle to the sound speed in the fluid. The acoustic radiation force acts in the direction of the acoustic field. The acoustic radiation force is proportional to the product of acoustic pressure and acoustic pressure gradient. An inspection of the acoustic radiation force shows that it is proportional to the particle volume, frequency (or wavenumber), the acoustic energy density (or the square of the acoustic pressure amplitude), and the acoustic contrast factor. Note also that the spatial dependency has twice the periodicity of the acoustic field. The acoustic radiation force is thus a function of two mechanical properties, namely density and compressibility.

TABLE 1

Properties of water and 4 selected secondary phases.

| Material | ρ (density) (kg/m³) | c (speed of sound) (m/s) | Λ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2.0 | 0.436 |

For three dimensional acoustic fields, a more general approach for calculating the acoustic radiation force is needed. Gor'kov's (1962) formulation can be used for this (see L. P. Gor'kov, "On the forces acting on a small particle in an acoustical field in an ideal fluid," Sov. Phys. Dokl., vol. 6, pp. 773-775, 1962). Gor'kov developed an expression for the acoustic radiation force $F_{ac}$ applicable to any sound field. The primary acoustic radiation force is defined as a function of a field potential U, given by $$F_{ac} = -\nabla(U), \quad (4)$$

where the field potential U is defined as $$U = V_0\left[\frac{\langle p^2(x,y,t)\rangle}{2\rho_f c_f^2}f_1 - \frac{3\rho_f\langle v^2(x,y,t)\rangle}{4}f_2\right], \quad (5)$$

and $f_1$ and $f_2$ are the monopole and dipole contributions defined by $$f_1 = 1 - \frac{1}{\Lambda\sigma^2}, \quad (6)$$

$$f_2 = \frac{2(\Lambda-1)}{2\Lambda+1},$$

where p(x,y,z,t) is the acoustic pressure and v(x,y,z,t) is the fluid particle velocity. $V_o$ is the volume of the particle.

The diagram 100 of FIG. 1 shows the force required to separate small particles of various material properties. Each material has its own X parameter given in Equation [3]. In diagram 100, material properties (e.g. speed of sound, density) are used for the indicated material. The graph for bacteria spore is also valid for other materials of similar bulk modulus. Meaning smaller bacteria spore, very large protein clusters, and polystyrene microspheres would all be in this category. The blood cell curve is for any cells of similar bulk modulus. Finally the hexane curve would be valid for any tiny drops of oil-like material with the radius indicated on the curve. These curves are for, as an example, 1 MHz applied acoustic frequency and an acoustic pressure of 0.5 MPa. These are easily achieved control variables. Higher frequency and higher pressure require better impedance matching and will afford better separation of smaller particles—down to 10 s of nm.

Figure 3:
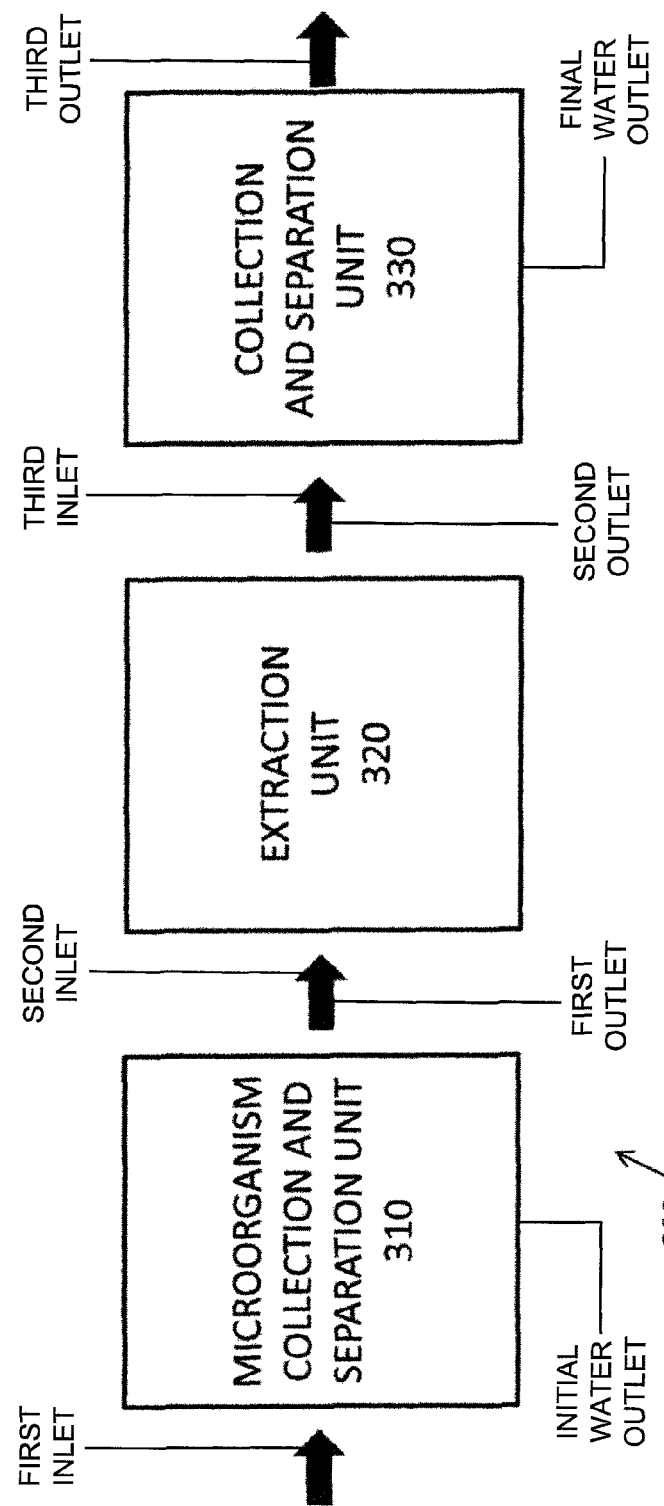
FIG. 3 is a block diagram illustrating a system including three sub-systems, namely a microorganism concentration and separation unit 310, a lipid extraction unit 320, and a lipid collection and separation unit 330.

FIG. 3 illustrates an overall system 300 to collect and process oleaginous microalgae for the production of biofuels that comprises three sub-systems. A microorganism concentration and separation unit 310 acoustophoretically concentrates and separates microorganisms from a host medium such as water. A lipid extraction unit 320 applies high intensity ultrasound to rupture the cell walls and cellular membranes of the microorganisms so that the lipid (i.e., biooil, etc.) content of the microorganisms is released into the water and an oil/water emulsion is formed. A lipid collection and separation unit 330 acoustophoretically concentrates and separates the water from the lipids, which were released by the microorganisms into water. The resulting oil layer can then be harvested for use as a feedstock for the production of biofuels or for other uses (e.g., carotenes as food supplements). While the current subject matter is mainly directed to microalgae, it is applicable to other types of microorganisms.

With regard to the microorganism concentration and separation unit 310, algae of the halophilic *Dunaliella Salina* were grown in a bottle filled with salt water and placed under a grow light. The algae were removed from the bottle through tubes that passed them into a flow channel and past an acoustic transducer. A sample apparatus is illustrated in diagram 400 of FIG. 4. With this arrangement, the flow chamber is horizontal with the transducer on top facing downward. Therefore, the resulting acoustic standing wave was in the vertical direction. The transducer was a PZT-4 2 MHZ transducer. A peristaltic pump was used to generate fluid flow rates that are most typically about 50 ml/min.

Figure 4:
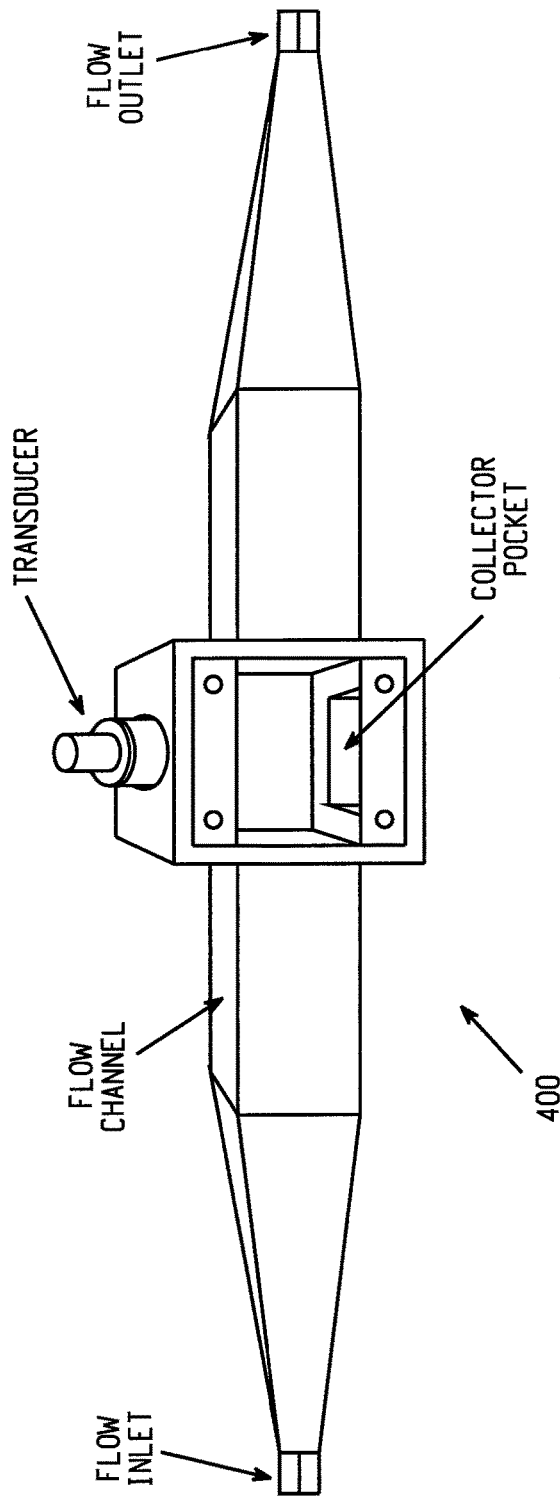
FIG. 4 is a diagram illustrating an apparatus having flow channels, acoustic transducer, reflective surface, and collection pocket, for the harvesting of microalgae through acoustophoretic trapping; the transducer is a 2 MHz PZT-4 transducers; the direction of the fluid flow is horizontal and the direction of the acoustic field is vertical.
Figure 5:
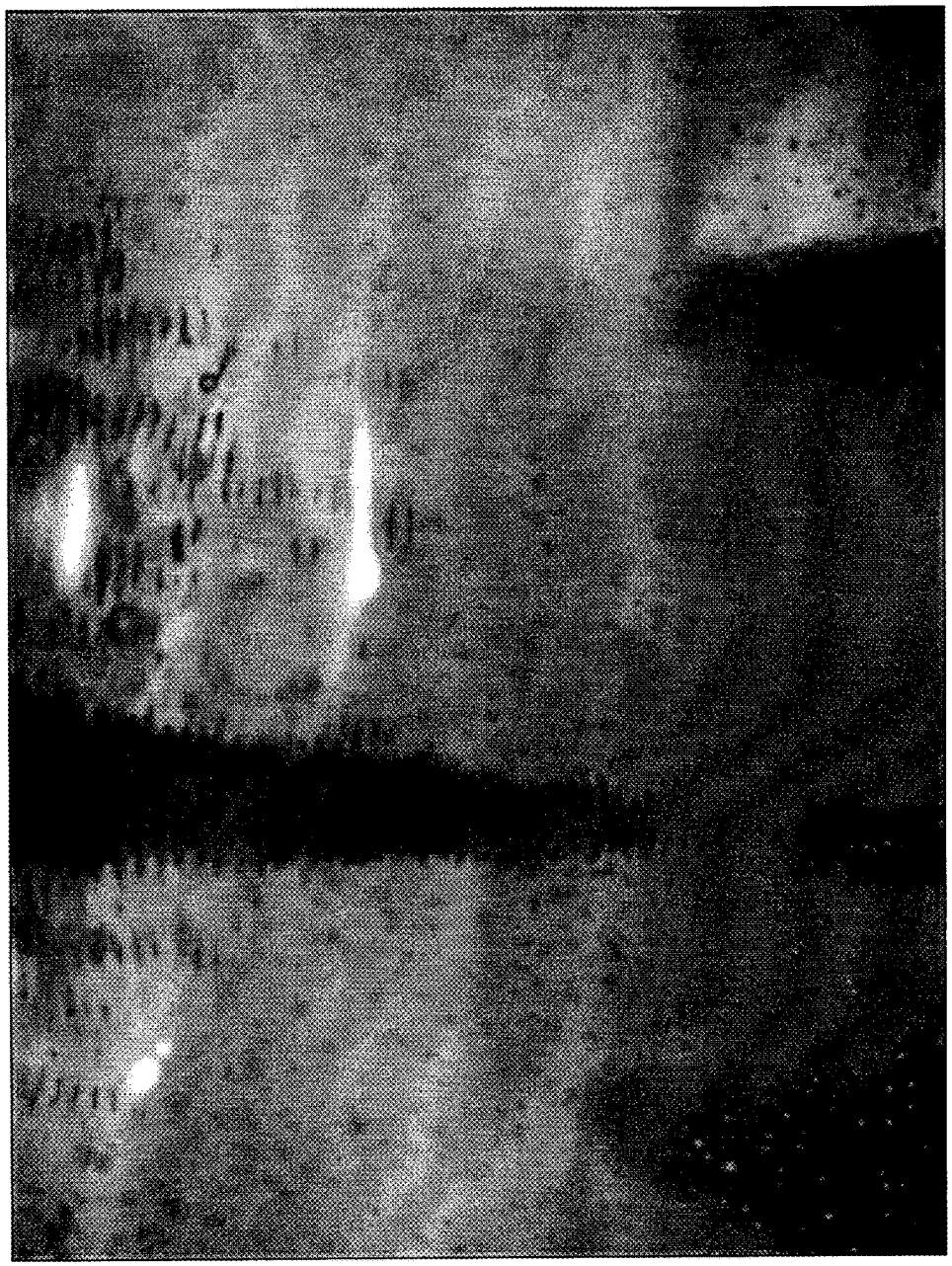
FIG. 5 is a photograph (at 10× magnification) of a typical collection of microalgae obtained using an apparatus such as illustrated in FIG. 4; the fluid flow direction is horizontal and the acoustic standing wave is in the vertical direction.

The acoustic transducer was connected to an amplifier which received its signal from a function generator and operated at about 15 Vrms. Once the fluid flow and the acoustic transducer were turned on, trapping and concentration of microalgae took place instantaneously. The microalgae were trapped in the acoustic field against the fluid drag force by means of the action of the acoustic radiation force. The collection of microalgae continued over time and eventually, typically after several minutes, large, beam-like collections of microalgae were seen in the region between the transducer face and the opposition reflective wall. A typical result of the acoustic trapping of microalgae for about 15 to 20 minutes in the system of FIG. 4 is shown in diagram 500 of FIG. 5.

Figure 6:
FIG. 6 is a series of three photos (at 10× magnification) of gravitational settling of the microalgae after the fluid flow has been stopped and the acoustic field has been turned off with the arrows indicate progression of time over 1 second intervals.

Two methods for the further separation and collection of the microalgae have been used, one is gravitational settling once the fluid flow has been stopped and the acoustic field has been turned off, as shown in diagram 600 of FIG. 6, and the second is the use of a frequency sweep method (see, for example, B. Lipkens, M. Costolo, and E. Rietman, "The effect of frequency sweeping and fluid flow on particle trajectories in ultrasonic standing waves", IEEE Sensors Journal, Vol. 8, No. 6, pp. 667-677, 2008) to translate and collect the microalgae in a collector pocket. For the first method the acoustic field has to be oriented along the vertical direction, for the second method there is no orientation constraint.

Figure 13:
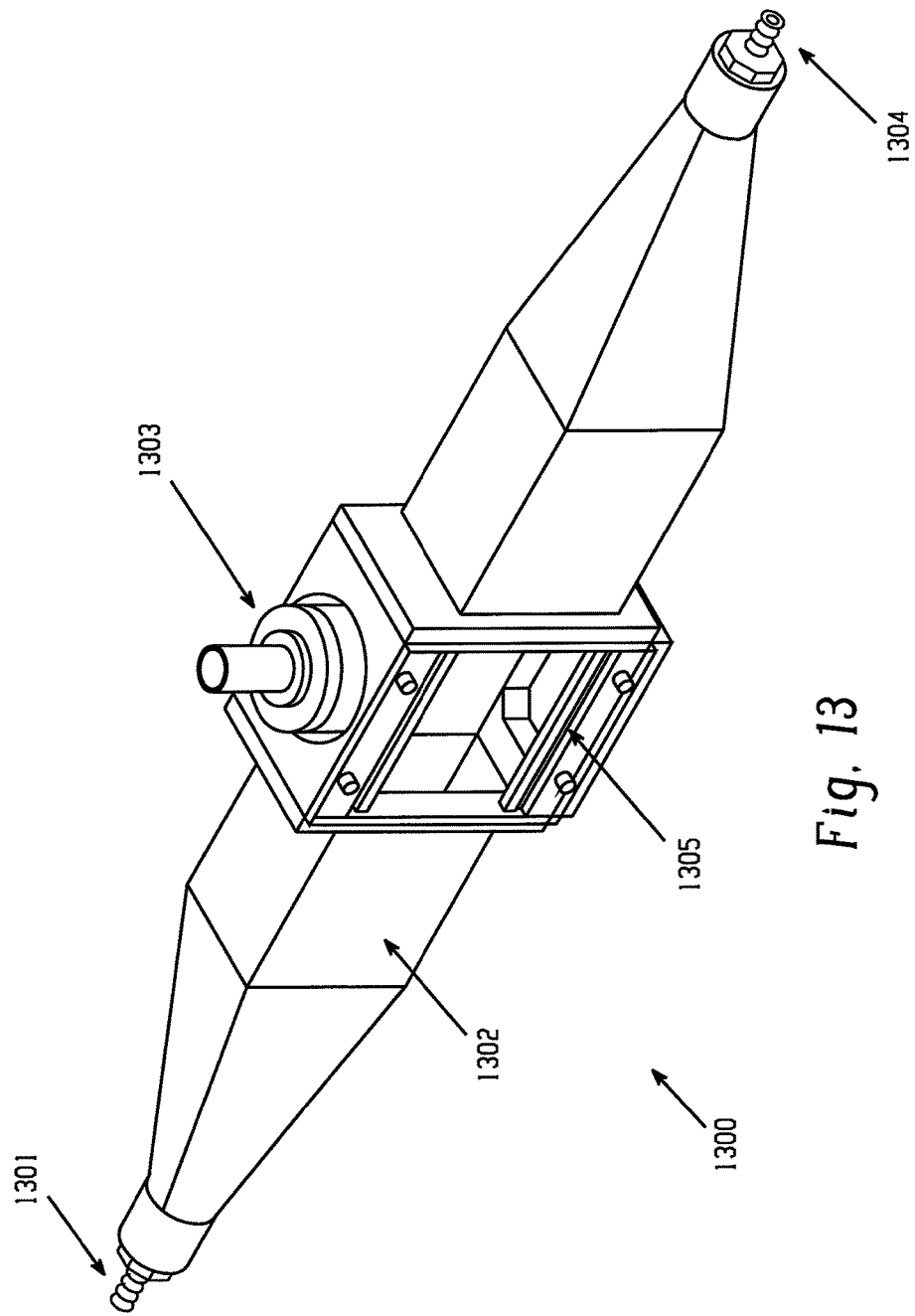
FIG. 13 is a diagram illustrating an apparatus for trapping, concentration, and collection of microorganisms and their separation from the host medium.

In one implementation of the microorganism concentration and separation unit 310, a flow channel within a flow chamber can be used to flow the fluid dispersion, typically water and a secondary-phase component that is dispersed in the water. See, for example, the diagram 1300 of FIG. 13 which illustrates a flow chamber 1302 having an inlet 1301 and an outlet 1304, at least one transducer 1303, and at least one corresponding reflector 1305. The secondary-phase component in this case is the microorganism of interest, e.g., microalgae. At least one ultrasonic transducer can be located in the wall of the flow channel. Piezoelectric transducers are often used. The transducer can be driven by an oscillating voltage that has an oscillation at an ultrasonic frequency. The ultrasonic frequency is typically in the range of several Megahertz and the voltage amplitude is on the order of tens of volts. The transducer, in combination with an acoustic reflection surface located at the wall of the flow tube opposite to the transducer, serves to generate an acoustic standing wave across the flow channel. Typical pressure amplitudes in the region of the acoustic standing wave or field are on the order of 0.5 MPa, amplitudes readily available with conventional piezoelectric transducers. The pressure amplitudes are below the cavitation threshold values so that a high intensity standing wave field is created without generation of cavitation effect or significant acoustic streaming. Acoustic streaming refers to a time-averaged flow of the water produced by the sound field. Typically, when acoustic streaming is generated it results in circulatory motion that may cause stirring in the water. Cavitation typically occurs when there are gas bodies, such as air micro-bubbles, present in the water. The effect of the sound pressure is to create micro-bubble oscillations which lead to micro-streaming and radiation forces. Micro-streaming around bubbles lead to shearing flow in the surround liquid. This flow contains significant velocity gradients. If a microorganism is located in this shearing flow, the uneven distribution of forces on the cell walls can lead to significant shear stresses exerted on the cell walls that may lead to cell wall disruption and rupture. At higher sound intensity levels, the micro-bubble oscillations become more intense, and the bubble can collapse leading to shock wave generation and free radical production. This is termed inertial cavitation.

Figure 14:
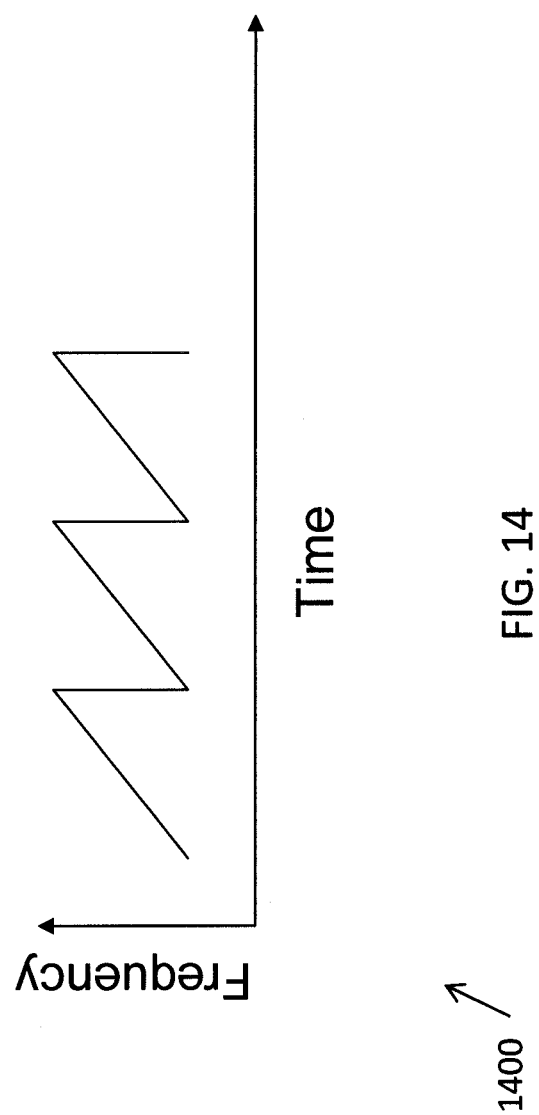
FIG. 14 is a diagram illustrating a frequency sweep pattern that can be used to translate trapped particles along the direction of the acoustic field.
Figure 15:
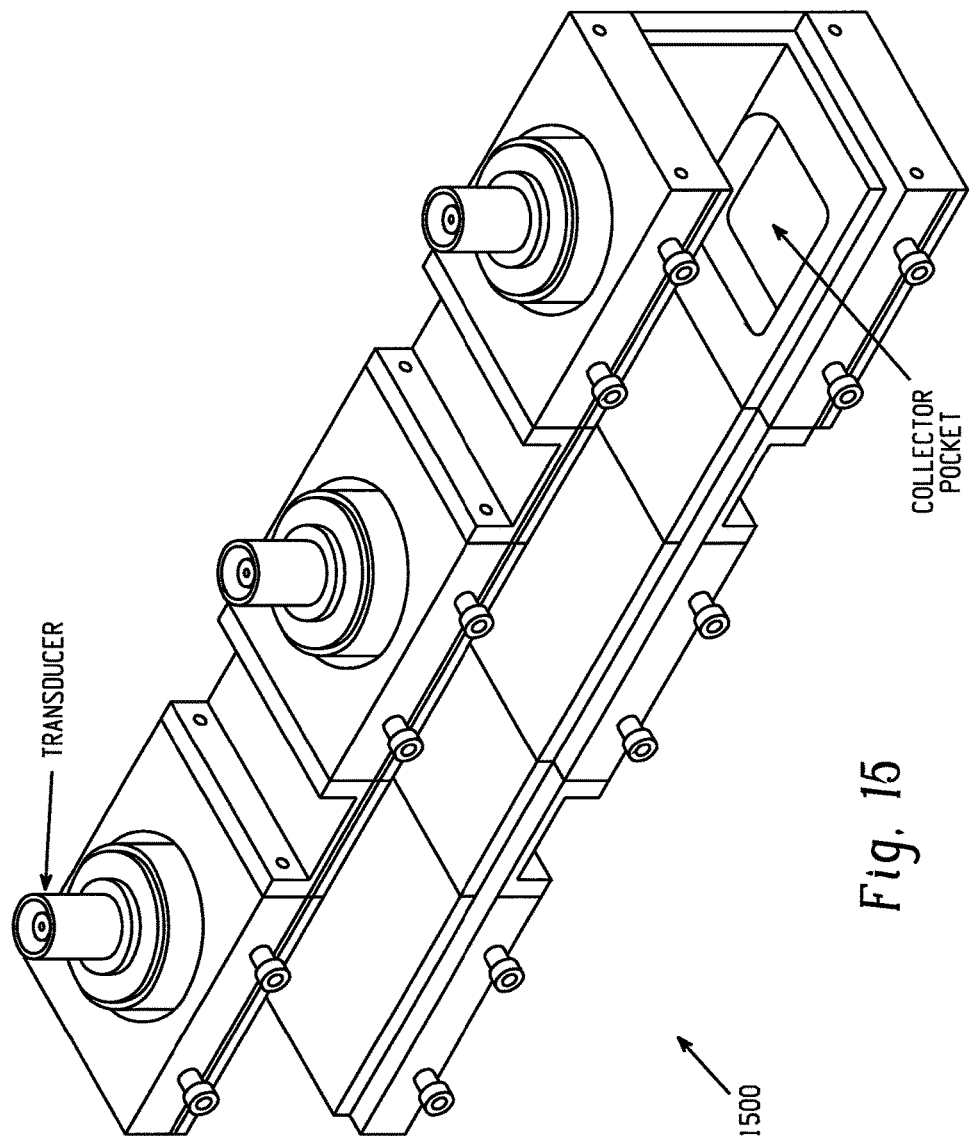
FIG. 15 is a diagram illustrating an apparatus for trapping, concentration, and collection of microorganisms and their separation from the host medium, containing multiple transducers in line.

The acoustophoretic force created by the acoustic standing wave on the secondary phase component, i.e., the microorganism, is sufficient to overcome the fluid drag force. In other words, the acoustophoretic force acts as mechanism that traps the microorganisms in the acoustic field. The acoustophoretic force drives the microorganisms to the stable locations of minimum acoustophoretic force amplitudes. Over time the collection of microorganisms grows steadily. Within minutes, depending on the concentration of the secondary phase component, the collection of microorganisms takes on the shapes of a beam-like collection of microorganisms consisting of disk-shaped collections of microorganisms, each disk spaced by a half wavelength of the acoustic field. The beam of disk-shaped collections of microorganisms is stacked between the transducer and the opposing, acoustically-reflective flow-tube wall. Therefore, acoustophoretic forces are able to trap and concentrate microorganisms in the region of the acoustic field while the host medium continues to flow past the concentrated microorganisms. The collection of microorganisms can continue until very large volumes of the host medium have been flowed through the trapping region and the capture of the containing microalgae has been attained. Further separation of the concentrated microorganisms from the host medium is achieved by two means. For a horizontal flow of the host medium, gravitational settling may be used to drive the concentrated microorganisms into collector pockets (see, for example, a collection pocket as illustrated in diagram 1500 of FIG. 15). For vertical or horizontal flow of the host medium, a slow frequency sweeping method may be used to translate the microorganisms into collector pockets (see, for example, diagram 1400 of FIG. 14). In this method, the frequency of the acoustic standing wave is slowly swept over a small frequency range, which spans at least a range of two frequencies corresponding to the one lower than the and one higher than the resonance of the standing wave mode of the cavity. The sweep period is typically on the order of seconds. This frequency sweeping method will slowly translate the collected microorganisms in the direction of the acoustic field towards one of the walls of the flow chamber where the microorganism may be collected for further processing. It will be appreciated that an array or differing types of transducers can be used (which in turn may operate at different or varying resonance frequencies).

Figure 7:
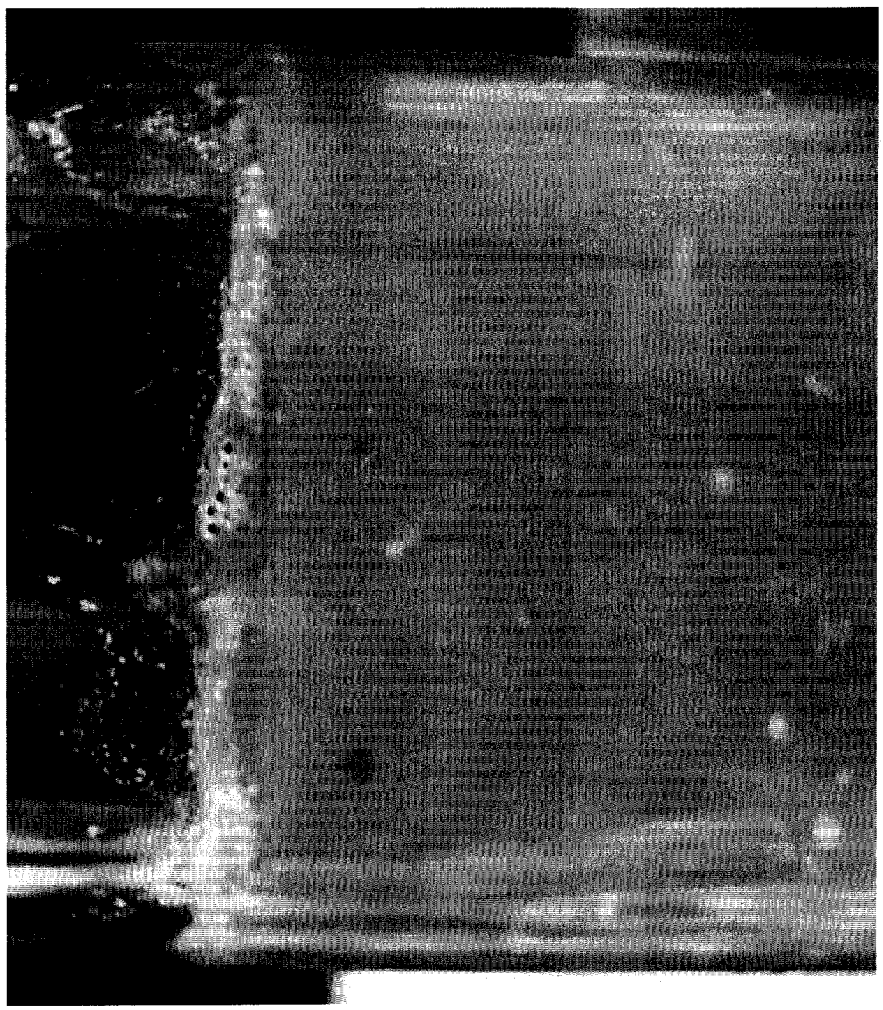
FIG. 7 is a photograph (at 10× magnification) showing cavitation occurring; the process is used to rupture the cell walls and the cellular membranes of the microalgae; cavitation is evidenced by the bubbles that form in the dispersion and have risen to the surface.
Figure 8:
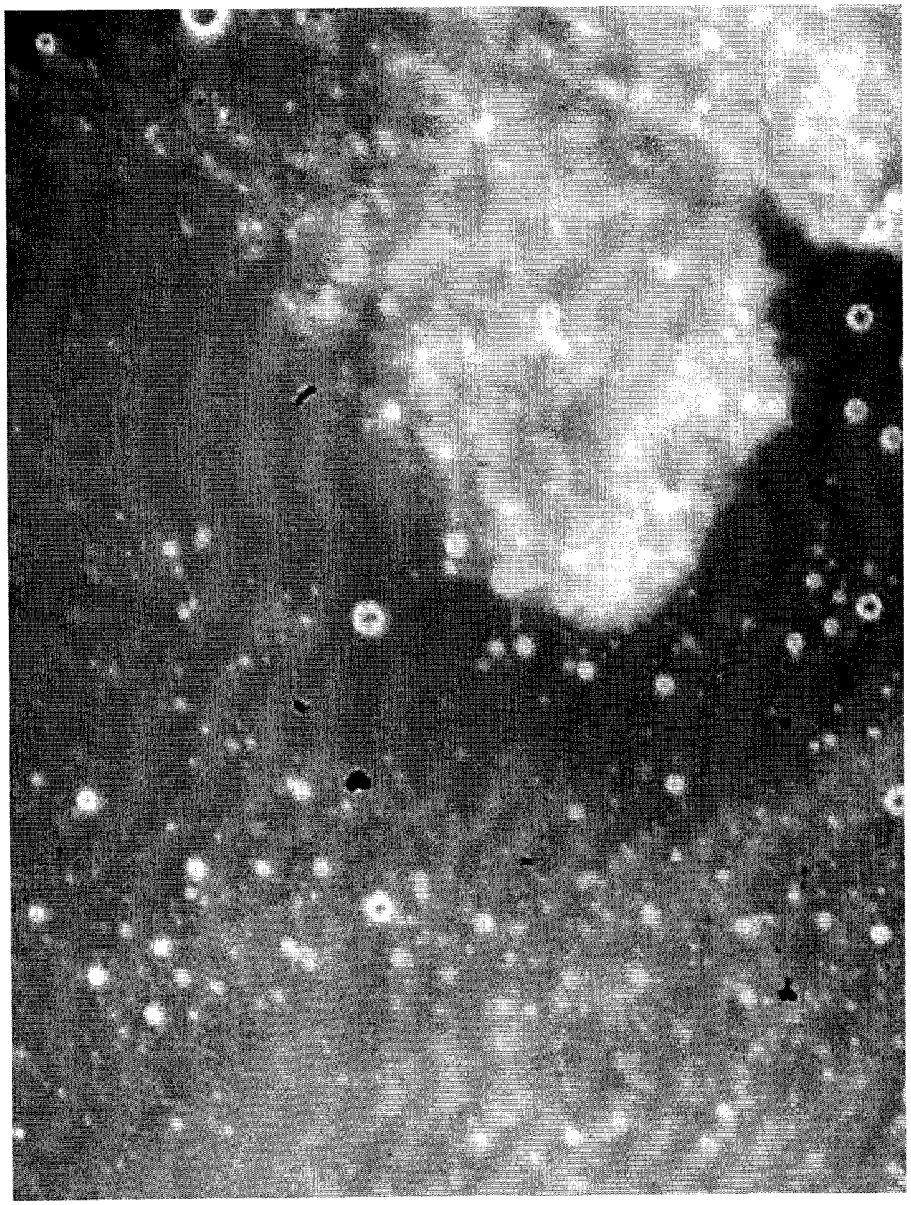
FIG. 8 is a photograph (at 400× magnification) of an oil/water emulsion obtained as a result of the cavitation process applied to a suspension of microalgae; typical oil droplet diameter is on the order of 3 μm.
Figure 18:
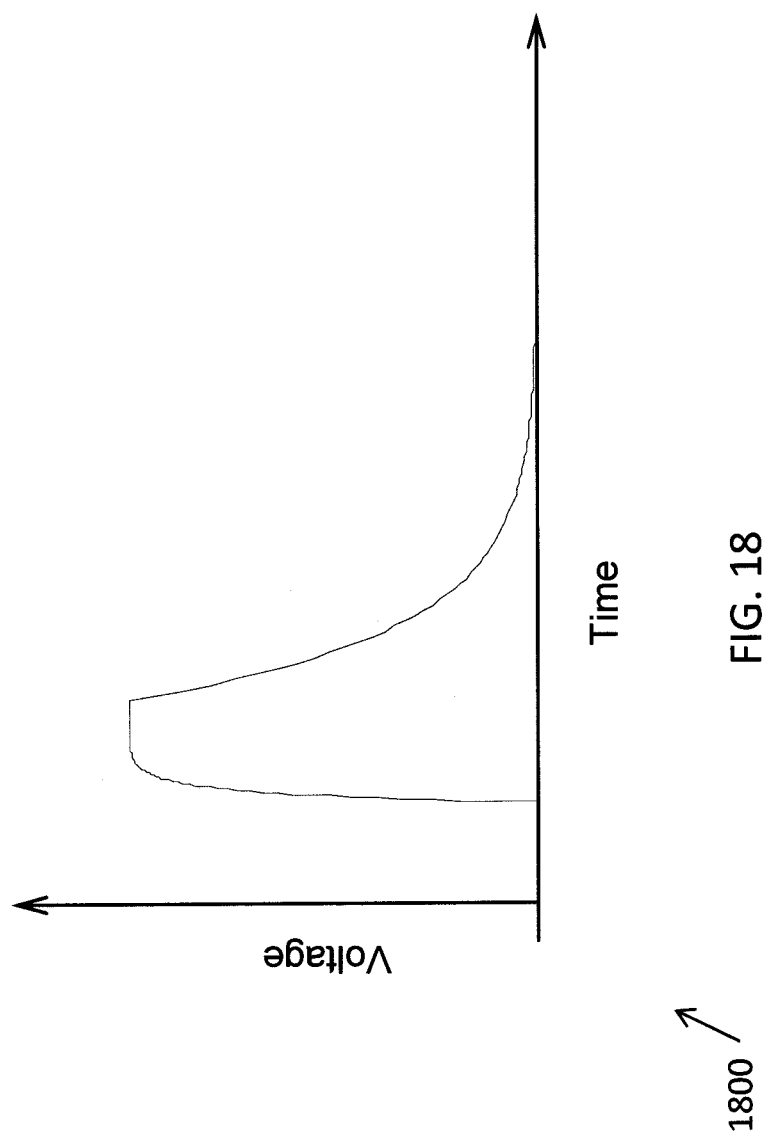
FIG. 18 is a diagram illustrating an arbitrary waveform that can be used in the rupturing process of the cell wall of the microorganisms.

With regard to the lipid extraction unit 320, two approaches can be used to extract the oil content from the microalgae. The first method is ultrasonic cavitation. The second method is the use of ultrasound of high intensity but not of cavitating amplitude to break the cell wall and cellular membranes of the microalgae (using, for example, an arbitrary waveform such as that illustrated in diagram 1800 of FIG. 18). A proof-of-concept demonstration was conducted in which a suspension of concentrated microalgae was put into a glass tube, six inches long and oriented vertically. A PZT-4 2.3 MHz transducer was mounted to the bottom. This system was used to cavitate the suspension of the microalgae in water, as shown in diagram 700 of FIG. 7. During the cavitation process, the cell wall and cellular membranes were ruptures and broken and the lipids were released from the cells. Typically, the acoustic field that results in cavitation was applied for about five minutes. Within a few minutes most of the microalgae debris—the cell wall and cellular debris which is darker green and light brown in color—falls to the bottom of the tube. The remaining dispersion was a clear, light green mixture. The lipids (oil) and the water are now in an emulsion, as seen in diagram 800 of FIG. 8. Typical oil droplet size was on the order of 3 µm in diameter.

Figure 16:
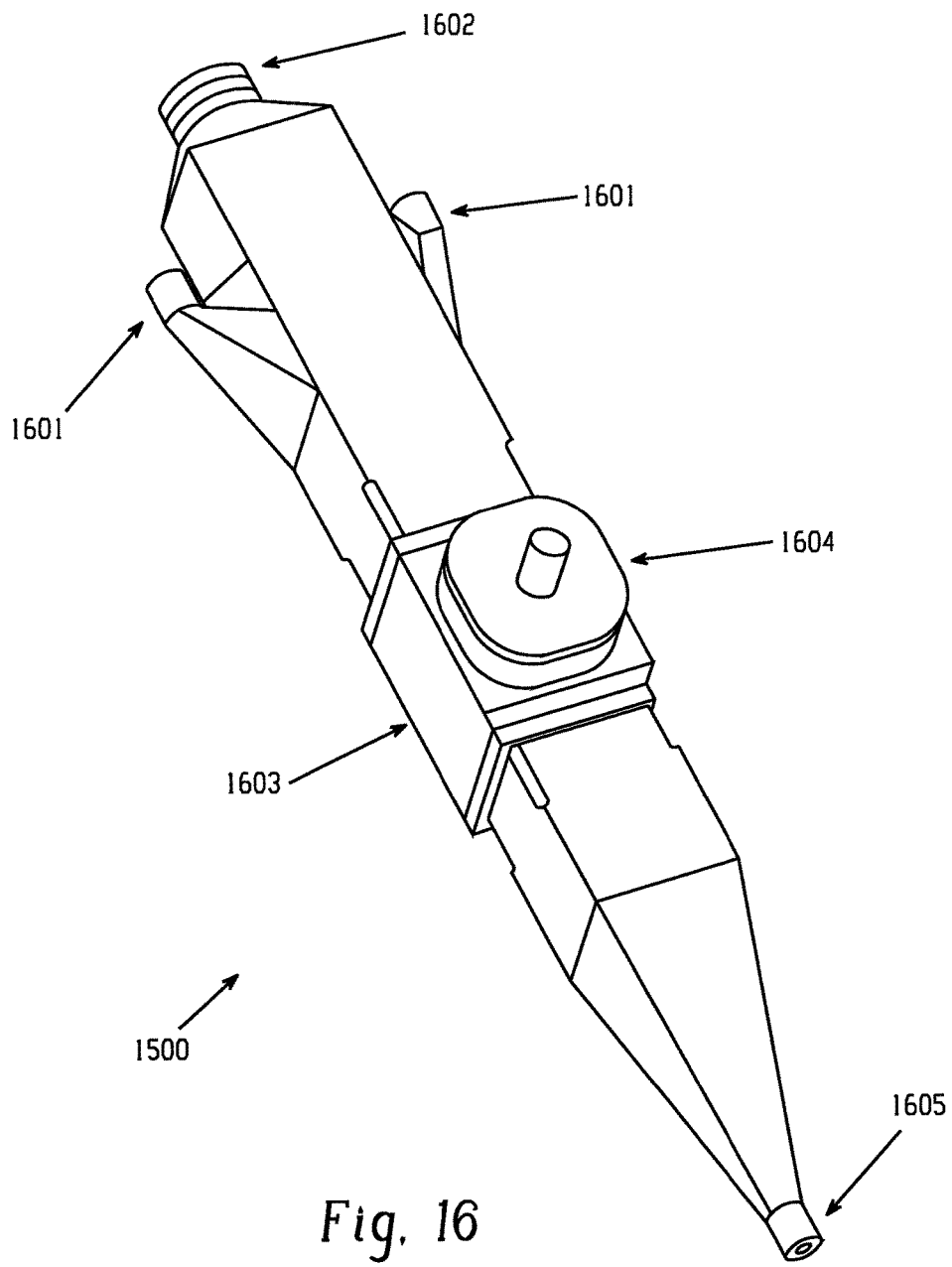
FIG. 16 is a diagram illustrating an apparatus for trapping, concentration, and separation of lipids/biooils from an oil/water emulsion.

The lipid extraction unit 320 comprises a vessel that is configured to rupture of the cell walls and cellular membranes of the microorganisms to release their lipid content. See, for example, diagram 1600 of FIG. 16 which provides a system including a flow chamber 1603 having at least one inlet 1601, a water outlet 1602, and a primary outlet 1605, at least one transducer 1604, and at least one corresponding reflector (not shown) that is on the wall opposing the transducer. In the wall of the vessel holding the microorganisms is at least ultrasonic transducer. The transducer can be driven by an oscillating voltage signal at ultrasonic frequencies typically in the kilohertz to Megahertz range. In one implementation, the transducer can be driven at voltages that generate acoustic standing waves of sufficient amplitude such that cavitation is generated. The result of cavitation occurring on the cell walls and membranes of the microorganisms is the generation of large shear forces of sufficient amplitude to rupture the cell wall and cellular membranes of the microorganisms. Once the cell wall is ruptured, the lipid content, i.e, the biooil, is released into the host medium, i.e., the water. This process results in an oil/water emulsion that also contains the cellular debris.

Figure 17:
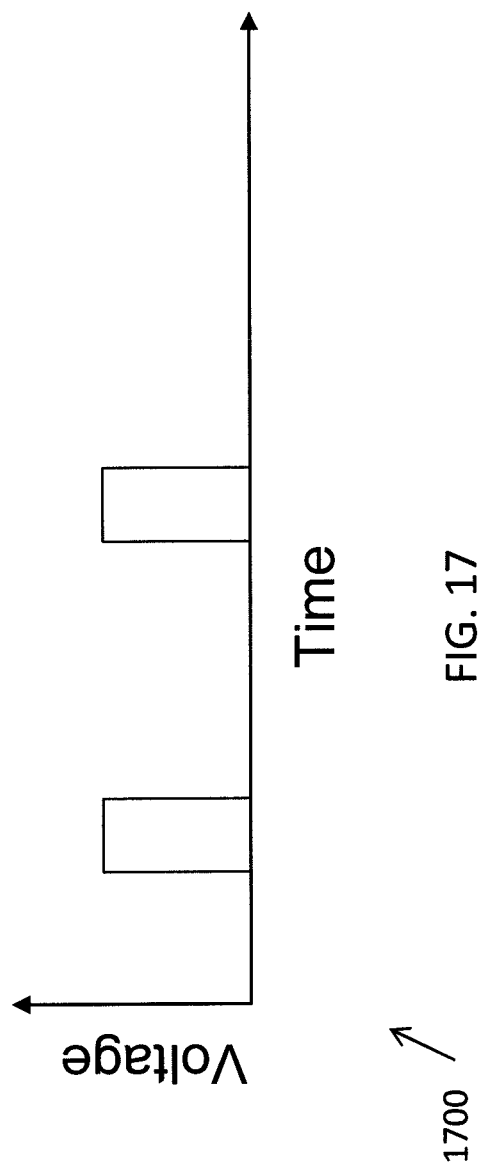
FIG. 17 is a diagram illustrating a pulsed waveform that can be used in the rupturing process of the cellular walls and membranes of the microorganisms.

In another implementation of the lipid extraction unit 320, the transducer can be driven by a pulsed voltage signal consisting of short-duration, large, positive-amplitude voltage spikes, followed by a longer duration of no applied voltage signal (see, for example, diagram 1700 of FIG. 17). This pulsed pattern can then repeated according to a pre-defined repetition rate or period. The effect of this excitation is to generate very large amplitude compressive pressure pulses in water that are sufficient to rupture the cell walls and cellular membranes of the microorganisms.

In another variation of the lipid extraction unit 320, the transducer can be driven by a pulsed voltage signal consisting of short-duration, large, negative-amplitude voltage spikes, followed by a longer duration of no applied voltage signal. This pulsed pattern can then be repeated according to a pre-defined repetition rate or period. The effect of this excitation is to generate very large amplitude expansion-type pressure pulses in water that are sufficient to rupture the cell walls and cellular membranes of the microorganisms.

The lipid extraction unit 320 can optionally include one or more variety of tanks such as those as shown in diagrams 1900-1930 of FIGS. 19A-19D. In the top two arrangements 1900, 1910, a recirculation system 1903 is employed in which a transducer 1901 (a flat transducer) or 1902 (a ring transducer) is within a tubular member extending from and back into a tank 1906. Within the tank 1906, host fluid enters via an inlet 1905 and exits via an outlet 1907 (such arrangement can be reversed depending on the desired configuration). In addition, within the tank 1906 there can be a plate transducer 1909 and/or an array transducer 1908 to further expose the host fluid to high intensity ultrasound.

With regard to the lipid collection and separation unit 330, a third proof-of-concept demonstration was conducted that demonstrated the coalescence, aggregation, concentration and separation of oil droplets from a stable oil/water emulsion. An emulsion was created to simulate an emulsion of microalgae lipids in water. A stable emulsion was created using water, baby oil, and Ceteareth-20. A fluid-flow apparatus was then used to separate the components of the emulsion, resulting in an oil layer and a water layer that are separate from one another.

Figure 9:
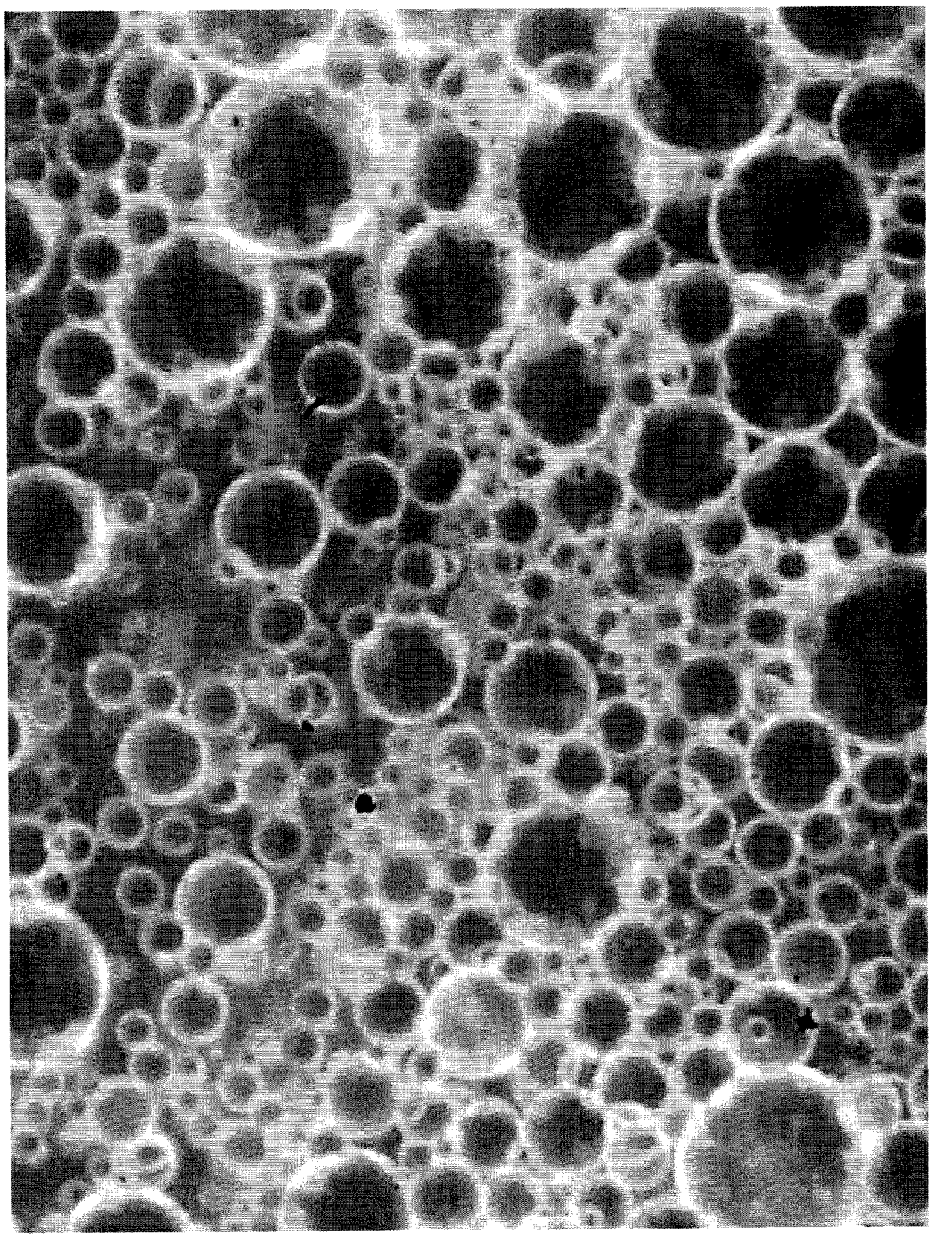
FIG. 9 is a photograph (at 400× magnification) of a stable emulsion made from 400 ml water, 10 ml baby oil, and four tablets of Ceteareth-20.

A stable emulsion was created from a mixture of four tablets of Ceteareth-20 (a common emulsifier), 400 mL of hot (180° F.) water, and 10 ml of baby oil. A photo, taken at 400× magnification, of the stable emulsion is shown in diagram 900 of FIG. 9. The oil droplets in the stable emulsion ranged in diameters from about three to six µm.

Figure 10:
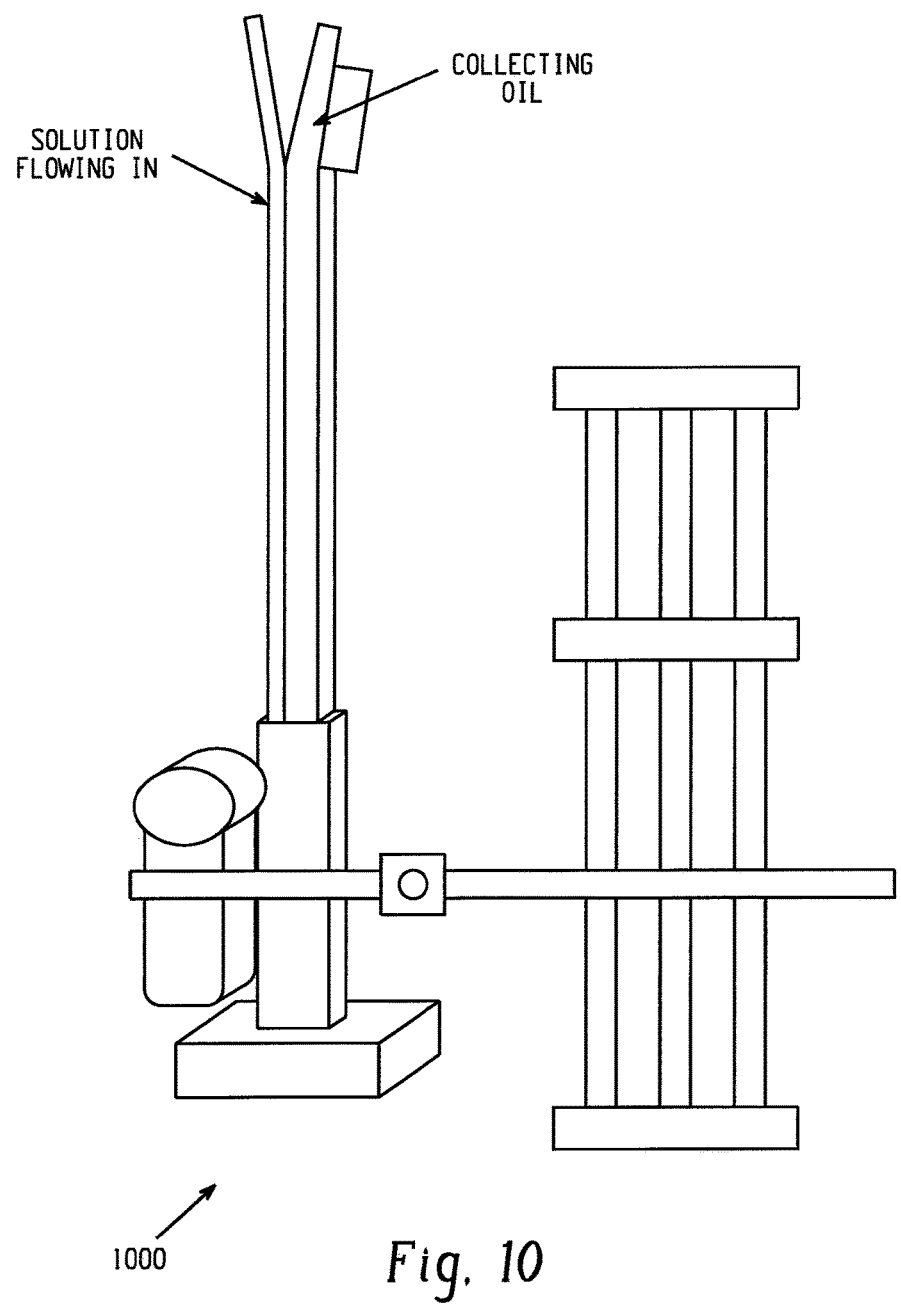
FIG. 10 is a photograph of an apparatus for oil concentration and separation; the stable emulsion flows through the region of the acoustic field in a downward vertical direction; the acoustic field is in the horizontal direction.

Next, a flow-through apparatus was used to concentrate and separate the oil phase from the emulsion. A photograph of the apparatus is shown in diagram 1000 of FIG. 10. The emulsion is flowing in a downward vertical direction. The acoustic field is perpendicular to the flow field, and acoustophoresis is used to trap the oil particles.

The transducer was a 2 MHz PZT-4 transducers, operating at 2 MHz and an applied voltage about 15 Vrms. The flow rate of the emulsion through the flow apparatus was on the order of 200 ml/min. After a typical trapping time of five minutes the fluid flow was stopped and the height of the oil layer that had been collected at the top of the chamber was measured.

Figure 11:
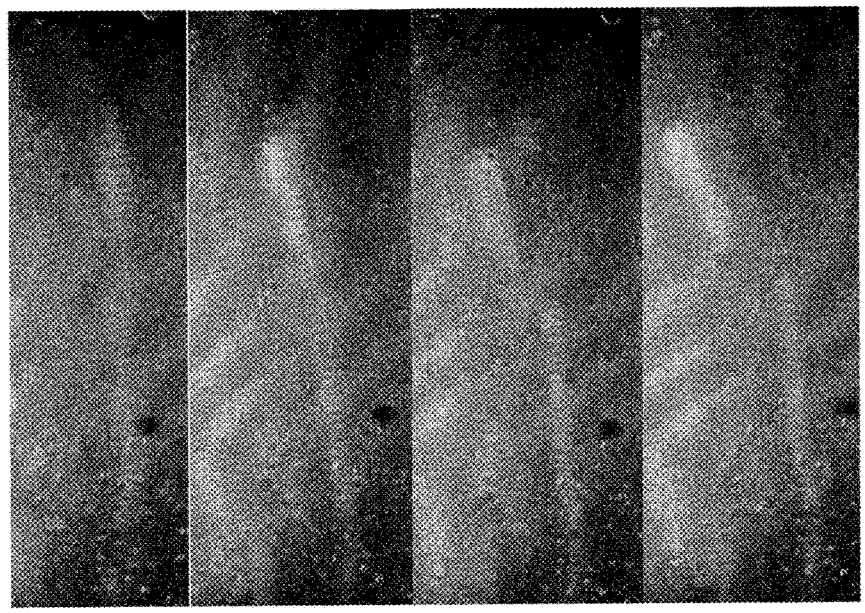
FIG. 11 is a series of four photos (at 10× magnification) showing the formation of oil droplet aggregates as a result of the trapping of the oil droplets in the acoustic field; the top-most photograph is the first in the time series; the bigger chain of oil droplets, formed as result of coalescence and agglomeration, has just started to rises as a result of buoyancy, and can be seen completely separated from the smaller line of oil droplets in the final, bottom-most photograph.
Figure 12:
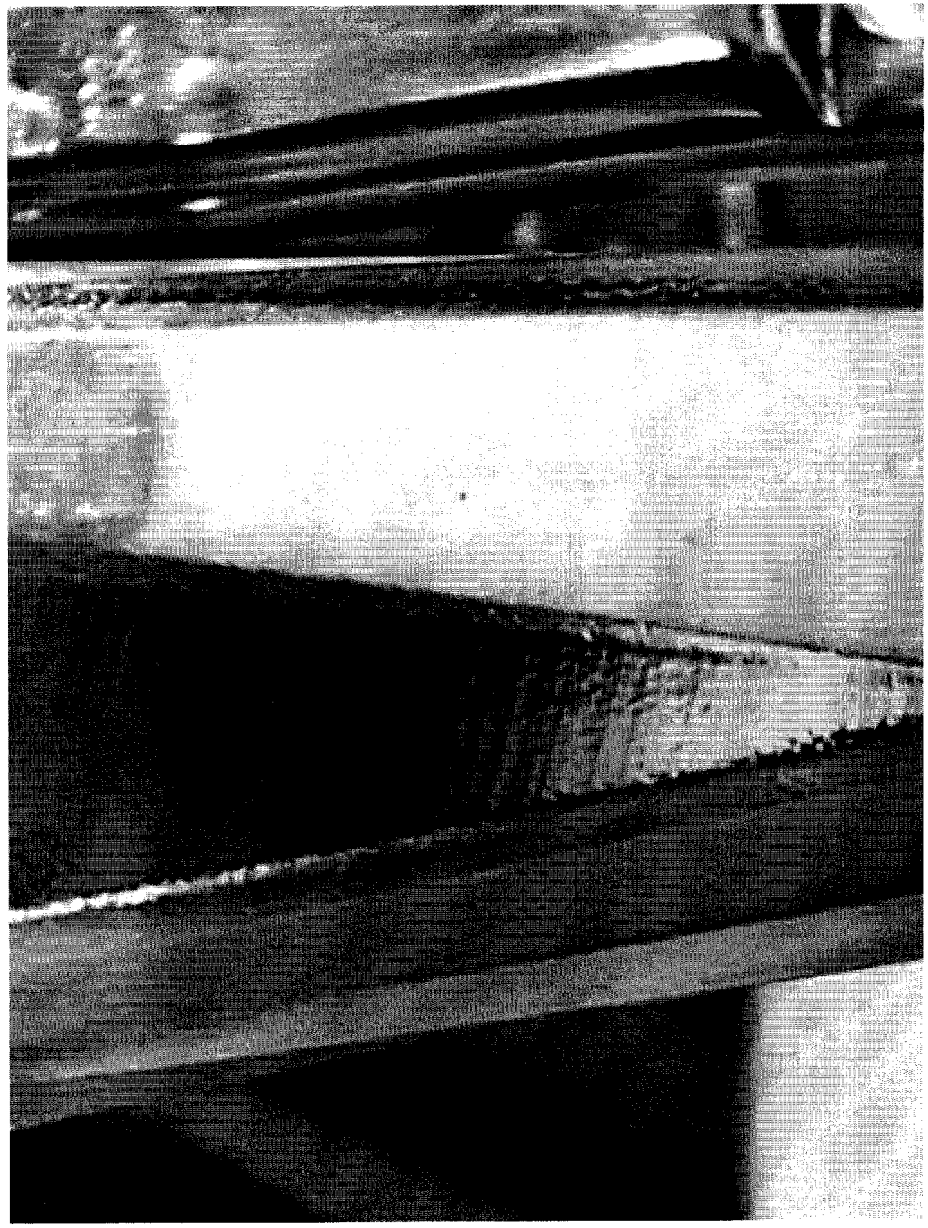
FIG. 12 is a photograph (10× magnification) of the collected oil layer at the top of the flow chamber as a result of the coalescence, aggregation, and concentration of the oil droplets.

Diagram 1100 of FIG. 11 shows the formation of oil droplets trapped in the acoustic field. Once the oil droplets are trapped, they coalesce to form bigger droplets, and agglomerate to form aggregates of the droplets. Once the aggregates have grown to a sufficient size, their buoyancy force drives the oil droplet aggregates to the surface of the chamber. Continuous formation of oil droplet aggregates is observed, followed by the rapid translation of the aggregates as a result of buoyancy. A second observation indicating rapid separation of the oil droplets from the water is from the visual observation of a cloudy solution above the transducer, (i.e., where the unprocessed emulsion has not yet passed through the acoustic field, but of a very clear solution below the transducer, where the oil has been removed by the acoustic field). These regions above and below the acoustic trapping region are separated by a sharp line between the cloudy solution and clear solution. After about 5 minutes of application of an acoustic trapping field while flowing the emulsion through the system, a layer of collected oil droplets is observed at the top of the chamber, as shown in diagram 1200 of FIG. 12.

The lipid collection and separation unit 330 can also include a flow channel is used to flow the oil/water emulsion. The flow direction of the emulsion is typically in the downward vertical direction. At least one ultrasonic transducer (e.g., a piezoelectric transducer, etc.) can be located in the wall of the flow channel and e driven by an oscillating voltage operating at an ultrasonic frequency, typically in the range of several Megahertz, and with voltage amplitude on the order of tens of volts. The transducer, in combination with an acoustic reflector located at the opposing wall of the flow tube, generates an acoustic standing wave across the flow channel. Typical pressure amplitudes are on the order of 0.5 MPa, amplitudes that are readily available with conventional piezoelectric transducers. The pressure amplitudes are below the cavitation threshold values so that a high-intensity standing-wave acoustic field is created without generation of cavitation effect or significant acoustic streaming. The acoustophoretic force created by the acoustic standing wave on the secondary phase component, i.e., the oil droplets, is sufficient to overcome the fluid drag force. In other words, the acoustophoretic force acts as mechanism that traps the oil droplets in the acoustic field. The acoustophoretic force drives the oil droplets to the stable locations of minimum acoustophoretic force amplitudes. Within seconds, depending on the concentration, the oil droplets form beam-like striations consisting of disk-shaped aggregates of oil droplets, each disk spaced by a half wavelength of the acoustic field; the disks are stacked between the transducer and the acoustic reflector. As soon as the oil aggregates reach a critical volume, the buoyancy force that the aggregate experiences is sufficient to drive the aggregates to the top of the fluid layer. Therefore, the acoustophoretic force acts as a concentrator of the oil droplets, causing coalescence and agglomeration of the droplets, and turning them into large aggregates of oil droplets, at which points buoyancy forces the oil aggregates to rise. Over time, a steadily increasing layer of separated oil, i.e., lipids, is collected at the top of the flow chamber. Various techniques can be employed to remove the oil layer.

While this specification contains many specifics, these should not be construed as limitations on the scope of what is claimed or of what may be claimed, but rather as descriptions of features specific to particular variations. Certain features that are described in this specification in the context of separate variations can also be implemented in combination in a single variation. Conversely, various features that are described in the context of a single variation can also be implemented in multiple variations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An apparatus comprising:
a microorganism collection and separation unit comprising a first flow chamber, the first flow chamber comprising:
a first inlet, a first outlet, and a initial water outlet, wherein an initial mixture of a host fluid and microorganisms enters through the first inlet;
at least one first ultrasonic transducer; and
a reflector surface opposite the at least one first ultrasonic transducer;
wherein the at least one first ultrasonic transducer operates to form a standing acoustic wave substantially perpendicular to the flow of the initial mixture to selectively separate the microorganisms from the host fluid, such that a majority of the host fluid exits the first flow chamber via the initial water outlet and the microorganisms and residual host fluid exit the first flow chamber via the first outlet;
operatively connected to the first outlet of the first flow chamber, an extraction unit comprising a second flow chamber, the second flow chamber comprising:
a second inlet through which is flowed the mixture of microorganisms and residual host fluid from the first outlet of the first flow chamber;
a second outlet; and
at least one second ultrasonic transducer forming a standing acoustic wave to selectively rupture cellular walls and membranes of the microorganisms and form cellular debris, the residual host fluid and cellular debris exiting the second flow chamber via the second outlet; and
operatively connected to the second flow chamber, a debris collection and separation unit comprising a third flow chamber, the third flow chamber comprising:
a third inlet through which is flowed the mixture of residual host fluid and cellular debris;
a third outlet and a final water outlet; and
at least one third ultrasonic transducer forming a standing acoustic wave substantially perpendicular to the flow of the mixture in the third flow chamber to selectively separate the cellular debris from the residual host fluid so that the cellular debris flows through the third outlet and the residual host fluid exits the third flow chamber via the final water outlet.

2. An apparatus as in claim 1, wherein the microorganisms are selected from the group consisting of: microalgae, yeast, fungi, bacteria, and spores.

3. An apparatus as in claim 1, wherein the at least one first ultrasonic transducer, the at least one second ultrasonic transducer, or the at least one third ultrasonic transducer operate at a frequency in a range of 1 MHz to 10 MHz.

4. An apparatus as in claim 1, wherein the at least one first ultrasonic transducer, the at least one second ultrasonic transducer, or the at least one third ultrasonic transducer are embedded in a wall of the corresponding flow chamber.

5. An apparatus as in claim 1, wherein the at least one first ultrasonic transducer, the at least one second ultrasonic transducer, or the at least one third ultrasonic transducer are driven at a constant frequency of excitation.

6. An apparatus as in claim 1, wherein the at least one first ultrasonic transducer, the at least one second ultrasonic transducer, or the at least one third ultrasonic transducer are driven by a frequency sweep pattern.

7. An apparatus as in claim 1, wherein the at least one first ultrasonic transducer is driven by a pulsed waveform that does not result in cavitation of the microorganisms.

8. An apparatus as in claim 1, wherein the at least one second ultrasonic transducer is driven by a waveform that results in cavitation of the microorganisms.

9. An apparatus as in claim 1, wherein the extraction unit further comprises a recirculation unit comprising a tank, an inlet, an outlet, at least one recirculation arm, and a transducer in either the tank or the at least one recirculation arm.

10. An apparatus as in claim 9, wherein the transducer is in the tank and is a plate transducer.

11. An apparatus as in claim 9, wherein the transducer is in the tank and is an array transducer.

12. An apparatus as in claim 9, wherein the transducer is in the at least one recirculation arm and is a flat transducer.

13. An apparatus as in claim 9, wherein the transducer is in the at least one recirculation arm and is a ring transducer.

14. An apparatus as in claim 1, wherein there are a plurality of transducers and each transducer is optimized for a specific range of particles selected from the group consisting of microalgae, yeast, fungi, bacteria, and spores.

15. An apparatus as in claim 1, wherein the at least one first ultrasonic transducer, the at least one second ultrasonic transducer, and the at least one third ultrasonic transducer operate at different frequencies from each other.

16. An apparatus as in claim 1, wherein the residual host fluid exiting the third flow chamber contains proteins and nucleic acids.

* * * * *